United States Patent [19]

Matsumoto et al.

[11] 4,424,274

[45] Jan. 3, 1984

[54] PROCESS FOR PRODUCING CITRIC ACID FROM HYDROCARBONS BY FERMANTATION

[75] Inventors: Takao Matsumoto; Yoshiyuki Ichikawa; Takeo Nagata, all of Yokohama, Japan

[73] Assignee: Showa Oil Company, Ltd., Tokyo, Japan

[21] Appl. No.: 375,465

[22] Filed: May 6, 1982

[30] Foreign Application Priority Data

Nov. 18, 1981 [JP] Japan ............................ 56-183656

[51] Int. Cl.$^3$ .......................... C12P 7/48; C12N 1/26; C12N 1/28
[52] U.S. Cl. .................................. 435/144; 435/248; 435/249; 435/818
[58] Field of Search ................ 435/144, 248, 249, 818

[56] References Cited

U.S. PATENT DOCUMENTS

| | | | |
|---|---|---|---|
| 3,308,035 | 3/1967 | Douros, Jr. ................... | 435/248 X |
| 3,912,585 | 10/1975 | Iijima et al. ................... | 435/818 X |
| 4,155,811 | 5/1979 | Nubel et al. ................... | 435/144 |
| 4,180,626 | 12/1979 | Nagata et al ................... | 435/144 |

Primary Examiner—Lionel M. Shapiro
Attorney, Agent, or Firm—Oldham, Oldham, Hudak, Weber & Sand Co.

[57] ABSTRACT

The present invention relates to a microbiological process for the production of citric acid by assimilation of α-olefins, normal paraffins and their mixture. This process is carried out by culturing the microorganisms selected from the group of *Candida tropicalis*, *Candida lipolytica*, *Candida intermedia* and *Canida brumptii* and their mutants and their variants under higher concentration of dissolved oxygen than that in ordinary aeration in the culture medium. The concentration of dissolved oxygen in the culture medium is suitable in the range of from 5 to 40 ppm, preferably from 10 to 30 ppm on the weight basis of said culture medium in this invention.

There is many means of which increase the dissolved oxygen in the culture medium. For example, in case of supplying a mixture of oxygen and air in the culture medium, the mixing ratio is suitable to from 2 parts to 25 parts of oxygen per 10 parts of air, preferably from 4 parts to 17 parts of oxygen per 10 parts of air by volume under normal temperature and pressure. It is important that the period maintaining the high concentration of dissolved oxygen in said culture medium should be immediately after the logarithmic growth phase of cultivation. Consequently, the productivity of citric acid is remarkably improved at high yield of more than 150 g/l in said fermentation process. α-olefins of $C_{8-40}$, normal paraffins of $C_{8-20}$ and their mixture are used as carbon source in this invention.

9 Claims, 3 Drawing Figures

PROCESS FOR PRODUCING CITRIC ACID FROM HYDRO

BACKGROUND OF THE INVENTION

The present invention relates to a microbiological process for producing citric acid from hydrocarbons. Particularly, this invention relates to the improvement of the productivity of citric acid from olefinic and paraffinic hydrocarbons as carbon source by culturing the microorganisms capable of assimilating hydrocarbons under aerobic conditions, wherein maintain higher concentration of dissolved oxygen in said culture medium than that in ordinary aeration by such means of supplying a mixture of oxygen and air.

The concentration of dissolved oxygen in the culture medium is less than 5 ppm bby weight in ordinary aeration of supplying atmospheric air only. However, in this invention, it is a characteristic feature that the concentration of dissolved oxygen in said culture medium is maintained in the range of from 5 to 40 ppm, preferably from 10 to 30 ppm on the weight basis of said culture medium.

There is many means of which increase the dissolved oxygen in the culture medium. For example, in case of supplying the mixture of oxygen and air in the culture medium, the mixing ratio is suitable to from 2 parts to 25 parts of oxygen per 10 parts of air, preferably from 4 parts to 17 parts of oxygen per 10 parts of air on the volume basis of each gas under normal temperature and pressure.

It has been well known that citric acid is produced by the assimilation of normal paraffins as carbon source. Furthermore, we, inventors, have been proposed the production process of citric acid from α-olefins of $C_{8-40}$ as carbon source by culturing the microorganisms selected from the group of *Candida tropicalis, Candida intermedia* and *Candida brumptii* and their mutants and their variants in U.S. Pat. No. 4,180,626.

Such α-olefins are easily obtained by thermal cracking of petroleum wax and by polymerization of ethylene. Said α-olefins, normal paraffins and their mixture are also used as carbon source in this invention.

We, inventors, have been accomplished that the productivity of citric acid in the fermentation of hydrocarbons under aerobic conditions is improved by increasing the concentration of dissolved oxygen in said culture medium by such means of supplying the mixture of oxygen and air.

SUMMARY OF THE INVENTION

This invention relates to the production process of citric acid by culturing the hydrocarbon assimilable microorganisms selected from the group of *Candida tropicalis, Candida lipolytica, Candida intermedia* and *Candida brumptii* and their mutants and their variants by accumulating citric acid in said culture medium and by recovering it. Particularly, it is a characteristic feature of this invention that the productivity of citric acid is remarkably improved by increasing the concentration of dissolved oxygen in the culture medium immediately after the logarithmic growth phase of culture by such means of supplying the mixture of oxygen and air under atmospheric condition in the cultivation.

Carbon sources used in this invention are α-olefins of $C_{8-40}$, normal paraffins of $C_{8-20}$ and their mixture. Olefins having carbon number of less than 13 are in great demand as the raw materials for plasticizers and synthetic detergents. However, olefins having carbon number of more than 14 are not marketable nowadays, and the present invention provides one of the profitable ways of promoting the effective utilization of such olefins. Normal α-olefins are preferable among olefins, but some iso- and inner-olefins are able to be used with normal α-olefins.

As the carbon source of α-olefins of $C_{8-40}$, it may be used the mixture of normal olefins produced from polymerization of ethylene by Ziegler's process, and the mixture of crude olefins produced by thermal cracking of petroleum wax under the conditions of cracking temperatures of 500°–650° C., of the liquid space velocity of 1–10 L.H.S.V. and of the molar ratio of water to wax of 5–10.

As said mixture of olefins are in liquid state at the fermentation temperature, good dispersion of said mixture of olefins can be maintained in the culture medium. The concentration of said hydrocarbons in the culture medium is suitable to from 1 to 20 percent, preferably from 5 to 15 percent on the weight basis of the culture medium.

When the aeration is carried out by supplying the mixture of oxygen and air, the mixing ratio of oxygen to air is from 2 parts to 25 parts of oxygen per 10 parts of air by volume at normal temperature and pressure in order to maintain the concentration of dissolved oxygen in the range of from 5 to 40 ppm on the weight basis of said medium. The producitivity of citric acid in said fermentation under the volume ratio of oxygen to air of less than 2 to 10 is not improved and is the same to that of supplying air only. Under the condition of the volume ratio of oxygen to air of more than 17 to 10, on the other hand, the productivity of citric acid is restrained.

As the nitrogen source of the culture medium, inorganic and organic ammonium salts, such as ammonium chloride, ammonium acetate, and various nitrogen compounds may be used individually or in mixture.

Ordinary inorganic salts such s phosphate, sulfate, chlorides, potassium salts, sodium salts, magnesium salts, iron salts, manganese salts, copper salts and zinc salts may be used as inorganic nutrients in culture medium. Calcium carbonate and alkali compounds may be used to regulate pH of said medium. Biotin and thiamine as organic nutrients may be used in a trace amount individually or in their mixture, and also natural substances such as yeast extract or corn steep liquor containing biotin and thiamine may be used. When biotin and thiamine are used individually, the amount of less than 1,000 μg/l of biotin or thiamine.HCl suffices to increase the production amount of citric acid. Even if the amount of more than 1,000 μg/l of biotin or thiamine is used individually, the production amount of citric acid does not increase. Preferable amount of the organic nutrients is suitable to from 50 to 100 μg/l. In case where both biotin and thiamine are added to said medium, the total amount of biotin and thiamine of less than 1,000 μg/l, preferably 50–100 μg/l is enough to cultivate.

The cultural conditions are shown as follows:

Said microorganisms are cultivated under aerobic conditions. The fermentation temperature is in the range of 25° and 40° C., preferably about 30° C. pH value of said medium is in the range of 3–10, preferably 4–6. pH value of said medium is regulated by adding alkalis or salts such as sodium carbonate or calcium carbonate. The cultivation is ordinarily carried out for 50–150 hrs., preferably 70–100 hrs. Citric acid accumulated in said medium is isolated in the form of calcium citrate by ordinary method, for example, by filteration or by centrifugal method and then purified by chromatographic or ion exchange method.

Figure 1:
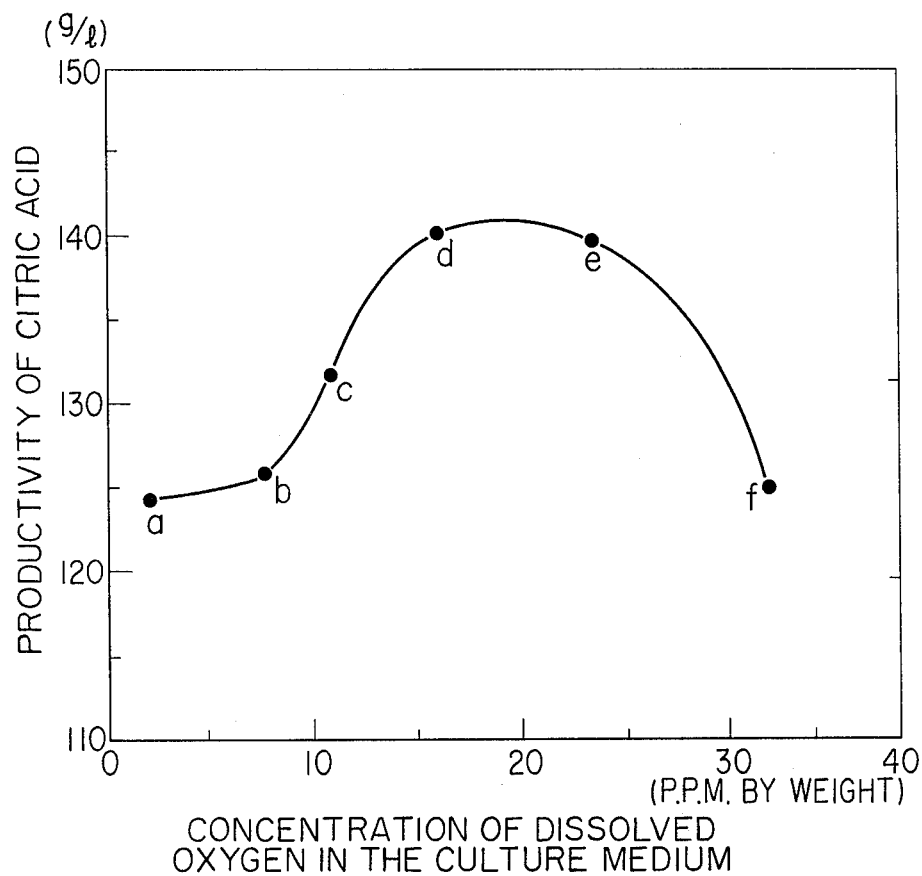
FIG. 1 shows the interrelationship between the concentration of dissolved oxygen and the productivity of citric acid in the culture medium containing n-octadecene-1 using microorganism of *Candida tropicalis*.

The axis of ordinate indicates the productivity of citric acid (g/l) in the culture medium, the abscissa indicates the concentration of dissolved oxygen in the culture medium (ppm by weight).

DETAILED DESCRIPTION OF THE INVENTION

The present invention relates to the production process of citric acid by culturing the hydrocarbon assimilable microorganisms selected the group of *Candida tropicalis, Candida lipolytica, Candida intermedia* and *Candida brumptii* and their mutants and their variants under aerobic conditions, wherein for example, the mixture of oxygen and air is supplied in the culture medium, and the mixing ratio of oxygen to air is in the range from 2 parts to 25 parts of oxygen per 10 parts of air by volume at normal temperature and pressure. Hereinafter are described the examples of the present invention. The process of the present invention is not limited by the following examples.

EXAMPLE 1

The composition of main culture medium is followed.
NH$_4$Cl: 0.3 (wt/vol%)
KH$_2$PO$_4$: 0.05 (wt/vol%)
MgSO$_4$.7H$_2$O: 0.03 (wt/vol%)
FeSO$_4$.7H$_2$O: 5 (mg/l)
MnSO$_4$.nH$_2$O: 0.06 (mg/l)
ZnSO$_4$.7H$_2$O: 0.05 (mg/l)
CuSO$_4$.5H$_2$O: 5 ($\mu$g/l)
Biotin: 50 ($\mu$g/l)
Thiamine.HCl: 100 ($\mu$g/l)
pH: 5.0

The citric acid fermentation was carried out by culturing *Candida tropicalis* IFO-0589 in said medium containing 10 weight percent of normal octadecene-1 (n-C$=$$_{18-1}$) as carbon source under aerobic conditions.

1.3 l of said culture medium contained in 2.6 l jar fermentor was sterilized at 115° C. for 10 minutes and allowed to cool at 30° C. The fermentation was carried out under the agitator speed of 1,000 rpm, and the aeration rate of 0.5 v.v.m. (volume of air/volume of medium/minute) at 30° C. of 4 days. 10N—NaOH aqueous solution was automatically added to said culture medium to regulate pH to 5.0.

Citric acid produced was recovered as follows:

Citric acid produced during the cultivation as described above was recovered in calcium salt form by filtering said medium using diatomaceous earth as a filter aid after conditioning pH to 2.0 with hydrochloric acid. The filter cake was washed with water, and the washing water was combined with the clear filtrate and then heated after neutralizing the combined filtrate by caustic alkali. The combined filtrate was cooled and filtrated under the reduced pressure to recover calcium citrate. Calcium citrate produced was suspended in about 10 times volume of water, and heated in the boiling water for about 30 minutes after titrating with 50% of aqueous sulfuric acid solution until the filtrate slightly indicate the presence of sulfuric acid with addition of the aqueous solution of barium chloride to said filtrate. If necessary, the resulting solution was filtered while heating after decoloring said filtrate and concentrated under the reduced pressure at the temperature of 50°–60° C. During concentrating said filtrate, the precipitated calcium sulfate was filtered and continued to the concentration until the slightly washy sirup was obtained. When the sirup-like concentrated liquor was allowed to cool at 0° C., the crystalline of citric acid was obtained.

The analysis of total citric acid was carried out as follows:

Citric acid was recovered from the culture medium as the calcium salt. The obtained salt was slurried with the distilled water and acidified to pH of less than 2 with hydrochloric acid to dissolve all soluble materials and was diluted with the distilled water to the predetermined volume.

Total citric acid (total amount of citric acid and isocitric acid) was quantitatively analyzed according to the modified Saffran method [Journal of Agricultural Chemical Society of Japan Bd. 44, Page 499 (1970)].

The interrelationship between the productivity of citric acid (g/l) and the concentration of dissolved oxygen (ppm) in said culture medium using *Candida tropicalis* was shown in FIG. 1. In FIG. 1, the curve showed the interrelationship between the productivity of citric acid and the concentration of dissolved oxygen in the culture medium under the conditions of supplying the mixtures of oxygen and air having the mixing volume ratios of oxygen to air of 2 to 10 (b), 4 to 10 (c), 6 to 10 (d), 8 to 10 (e) and 17 to 10 (f) respectively. The symbol (a) in FIG. 1 indicated the productivity of citric acid in case of supplying air only in the culture medium. The greatest increase in citric acid production is obtained when the oxygen concentration is maintained at high level after the logarithmic growth phase of the microorganisms.

As being clarified from the curve in FIG. 1, the productivity of citric acid reached to 130–140 g/l when mixed gas of oxygen and air ranging of from 2 parts to 17 parts of oxygen per 10 parts of air by volume was supplied, and the concentration of dissolved oxygen in the said culture medium was kept from 10 to 30 ppm. However, the yield of citric acid was not increased when said mixing ratio of oxygen to air exceeded the ratio of 17 to 10.

*Candida tropicalis* IFO-0589 was employed as the microorganism in Example 1 of this invention. Moreover, the same results were obtained by using the microorganisms selected from *Candida intermedia* and *Candida brumptii*.

EXAMPLE 2

Figure 2:
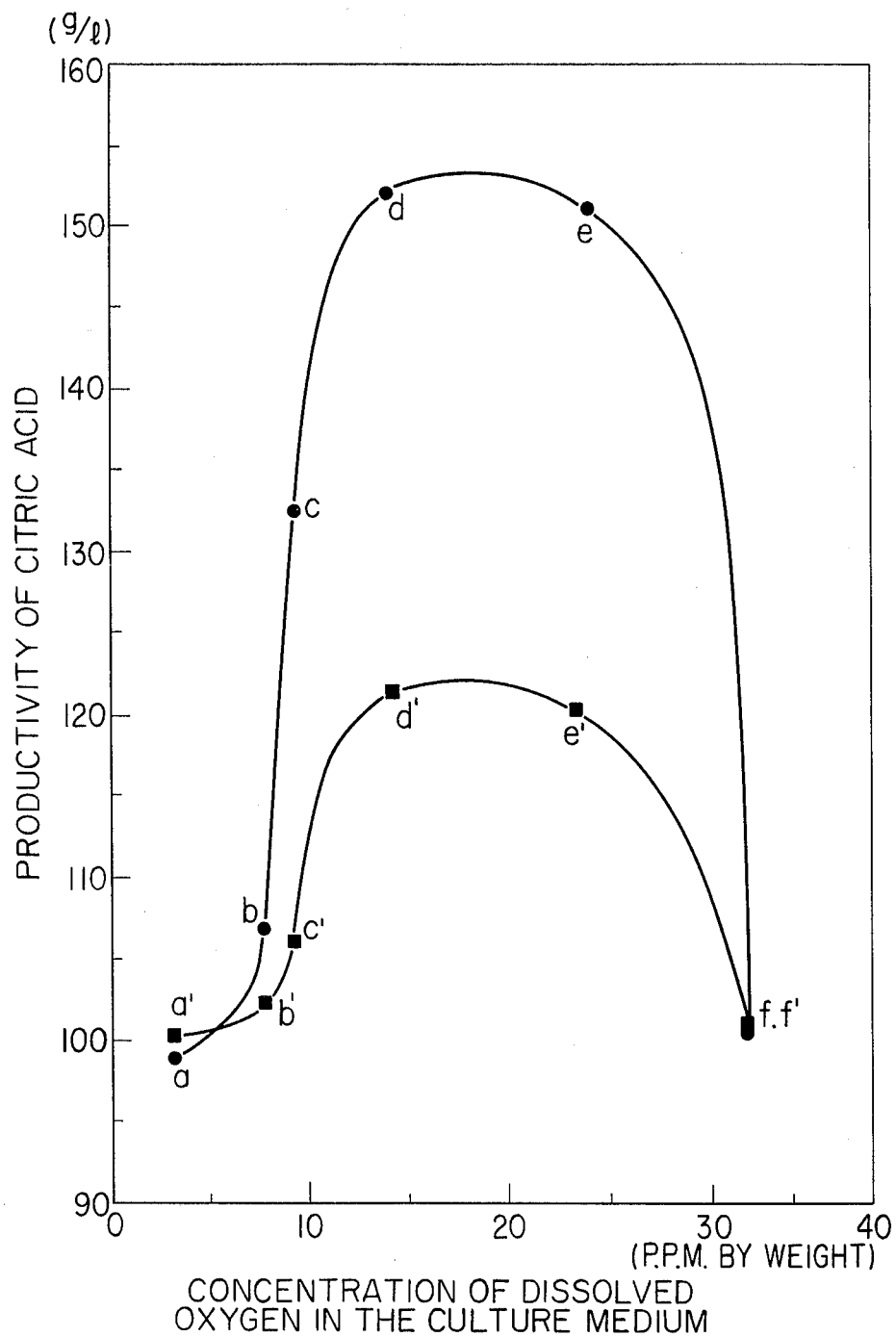
FIG. 2 shows the interrelationship between the concentration of dissolved oxygen and the productivity of citric acid in the culture medium containing n-Hexadecane using the microorganisms of *Candida tropicalis* and *Candida lipolytica* respectively.

The citric acid fermentation was carried out by culturing *Candida lipolytica* IFO-0746 and *Candida tropicalis* IFO-0589 in the culture medium containing 10 weight percent of normal hexadecane (n-$C_{16}$) as carbon source under the same conditions to those of the process of Example 1. The results were shown in FIG. 2. In FIG. 2, the curves showed the interrelationship between the productivity of citric acid and the concentration of dissolved oxygen in the culture medium under the conditions of supplying the mixtures of oxygen and air having the mixing volume ratio of oxygen to air of 2 to 10 (b, b'), 3 to 10 (c, c'), 5 to 10 (d, d'), 8 to 10 (e, e') and 17 to 10 (f, f') respectively. The symbols a, b, c, d, e and f indicated the productivity of citric acid in case of using the microorganism of *Candida tropicalis*, while the symbols a', b', c', d', e' and f' indicated the productivity of citric acid in case of using the microorganism of *Candida lipolytica*. The symbols a and a' indicated the productivity of citric acid in case of supplying air only in the culture medium. From FIG. 2, it was proved that the yield of citric acid reached to more than 150 g/l.

EXAMPLE 3

Figure 3:
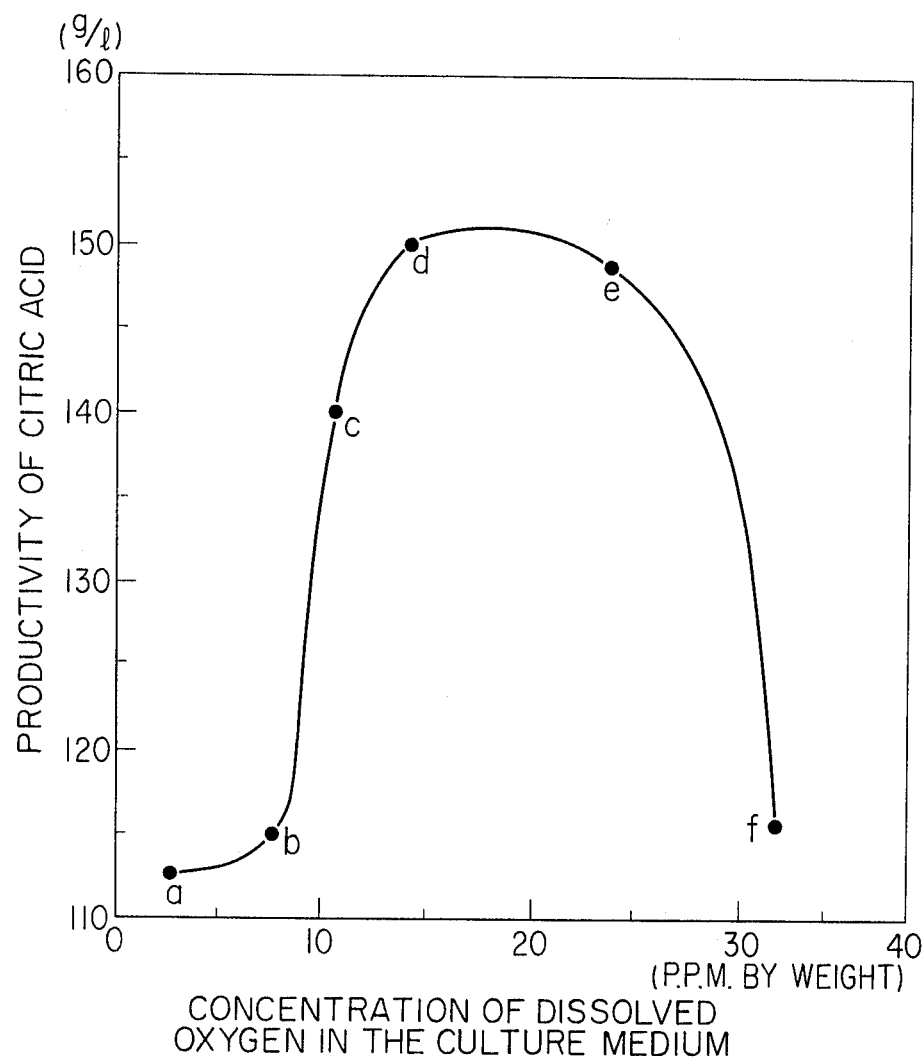
FIG. 3 shows the interrelationship between the concentration of dissolved oxygen and the productivity of citric acid in the culture medium containing the mixture of n-octadecene-1 and n-Hexadecane (1 to 1 by weight) using the microorganism of *Candida tropicalis*.

The citric acid fermentation was carried out by culturing *Candida tropicalis* IFO-0589 in the culture medium containing 10 wt% of the mixture of n-octadecene-1 and n-hexadecane as carbon source under the same conditions to those of the process of Example 1, wherein the mixing ratio of n-octadecene-1 to n-hexadecane was 1 to 1 by weight. The results were shown in FIG. 3. From FIG. 3, it was proved that the productivity of citric acid reached to more than 150 g/l. In FIG. 3, the curved showed the interrelationship between the productivity of citric acid and the concentration of dissolved oxygen in the culture medium under the conditions of supplying the mixtures of oxygen and air having the mixing volume ratios of oxygen to air of 2 to 10 (b), 4 to 10 (c), 5 to 10 (d), 8 to 10 (e) and 17 to 10 (f) respectively. The symbol a indicated the productivity of citric acid in case of supplying air only in the culture medium.

What is claimed is:

1. A process for producing citric acid by fermentation which comprises:
    culturing the hydrocarbon assimilable microorganisms selected from *Candida tropicalis, Candida lipolytica, Candida intermedia* and *Candida brumptii* and their mutants and their variants under aerobic conditions, while maintaining a concentration of dissolved oxygen in the culture medium of from about 15 to about 40 parts per million on a culture medium weight basis immediately after the logorithmic growth phase of the cultivation, at a temperature from about 25° C. to about 40° C. and at a pH from about 3 to about 10 in a culture medium containing hydrocarbons selected from olefinic and paraffinic hydrocarbons and their mixture, and recovering the produced citric acid from said culture mixture.

2. The process according to claim 1 wherein the concentration of dissolved oxygen in said culture medium is in the range of from about 10 parts to about 30 parts per million on the weight basis of the culture medium.

3. The process according to claim 2, wherein in case of supplying the mixture of oxygen and air in the culture medium, the mixing ratio of oxygen and air is from 2 parts to 25 parts of oxygen per 10 parts of air by volume under normal temperature and presure condition.

4. The process according to claim 1, wherein hydrocarbons used as carbon source are selected from the group consisting of normal α-olefins of carbon number of 8 to 40, normal paraffins of carbon number of from 8 to 20 and their mixture.

5. The process according to claim 4, wherein the assimilable carbon source is the mixture of α-olefins of $C_{8-40}$ produced by thermal cracking of petroleum wax under the conditions of cracking temperature of 500°–650° C., of the liquid space velocity of 1–10 L.H.S.V. and of the molar ratio of water to wax of 5–10.

6. The process according to claim 4, wherein the assimilable carbon source is the mixture of α-olefins of $C_{8-40}$ produced by polymerization of ethylene.

7. The process according to any one of claims 1, 4, 5 and 6, wherein the amount of olefins, paraffins and their mixture added as carbon source to the culture medium is 1–20% on the weight basis of said culture medium.

8. A process according to claim 6, wherein said mixing ratio of oxygen and air is from about 4 to about 17 parts of oxygen per 10 parts of air by volume under normal temperature and pressure conditions, and wherein the amount of said hydrocarbons in said culture medium is from about 5 to about 15% by weight of said medium.

9. A process according to claim 8, wherein the amount of said hydrocarbons used as a carbon source is from about 5 to about 15% on the weight basis of said culture medium.

* * * * *